United States Patent [19]
Pettit et al.

[11] Patent Number: 5,801,222
[45] Date of Patent: Sep. 1, 1998

[54] ISOLATION AND STRUCTURE OF THE HUMAN CANCER CELL GROWTH INHIBITORY CYCLIC OCTAPEPTIDES PHAKELLISTATIN 10 AND 11

[75] Inventors: George R. Pettit, Paradise Valley; Rui Tan, Mesa, both of Ariz.

[73] Assignee: Arizona Board of Regents acting on behalf of Arizona State University, Tempe, Ariz.

[21] Appl. No.: 360,239

[22] Filed: Dec. 20, 1994

[51] Int. Cl.$^6$ .............................. C07K 7/64; A61K 38/12
[52] U.S. Cl. .................. 530/317; 514/11; 514/9; 514/2
[58] Field of Search ............... 514/11, 9, 2; 530/317

[56] References Cited

PUBLICATIONS

Tsula, Tetarahedron, vol. 50, No. 16, pp. 4667–4680, (1994)
Pettit et al, Journal of Natural Products, vol. 56, No. 2, pp. 260–267, (Feb. 1993).
Pettit et al, J. Org. Chem., vol. 57, pp. 7217–7220, (1992).
Pettit et al, Bioorganic & Medicinal Chem., vol. 4, No. 17, pp. 2091–2096, (1994).

*Primary Examiner*—Ponnathapura Achutamurthy
*Assistant Examiner*—T. D. Wessendorf
*Attorney, Agent, or Firm*—Richard R. Mybeck

[57] ABSTRACT

Two new compounds which may be useful in the treatment of one or more neoplastic diseases through chemotherapy have been isolated from the Western Pacific Ocean marine sponge Phakellia sp. The cyclic octapeptides phakellistatin 10 and phakellistatin 11 are disclosed herein.

As the included data demonstrate, phakellistatin 10 attained an $LC_{50}$ of less than $10^{-5}M$ per milliliter against the MDA-MB-435 breast cancer cell line. It also achieved total growth inhibition for two breast cancers and two CNS cancer cell lines at a concentration of less than $10^{-6}M$ per milliliter. The included data for phakellistatin 11 shows a moderately higher level of in vitro activity as shown by an $LC_{50}$ of less than $10^{-5}M$ per milliliter against the MDA-MB-435 breast cancer cell line and five other cell lines. It also achieved total growth inhibition for two breast cancers, one CNS cancer, one Ovarian cancer, and one non-small cell lung cancer cell lines at a concentration of less than $10^{-7}M$ per milliliter.

4 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 8 amino acid residues
        ( B ) TYPE: amino acid
        ( D ) TOPOLOGY: Cyclic ( i i ) MOLECULE TYPE:
        ( A ) DESCRIPTION: Cyclooctapeptide phakellistatin 10

( i i i ) HYPOTHETICAL: no ( i v ) ANTI-SENSE: no ( v ) FRAGMENT TYPE: circular ( v i ) ORIGINAL SOURCE:
        ( A ) ORGANISM: Phakellia sp.
        ( D ) DEVELOPMENTAL STAGE: whole organism ( i x ) FEATURE:
        ( A ) NAME/KEY: Phakellistatin 10
        ( c ) IDENTIFICATION METHOD: by experiment using amino acid analysis, high resolution nuclear magnetic resonance and mass spectral MS/MS techniques
        ( D ) OTHER INFORMATION: Phakellistatin 10 is a cell growth inhibitory peptide with activity in murine lymphocytic leukemia cell line of 2.1 mg/mL ( x i ) SEQUENCE DESCRIPTION: SEQ ID NO: 1:

Pro Leu Thr Pro Ile Pro Trp Val
        1                    5

( 2 ) INFORMATION FOR SEQ ID NO:2:

( i ) SEQUENCE CHARACTERISTICS:
        ( A ) LENGTH: 8 amino acid residues
        ( B ) TYPE: amino acid
        ( D ) TOPOLOGY: Cyclic

```
( i i ) MOLECULE TYPE:
        ( A ) DESCRIPTION: Cyclooctapeptide
              phakellistatin 11

( i i i ) HYPOTHETICAL: no ( i v ) ANTI-SENSE: no ( v ) FRAGMENT TYPE: circular ( v i ) ORIGINAL SOURCE:
        ( A ) ORGANISM: Phakellia sp.
        ( D ) DEVELOPMENTAL STAGE: whole organism ( i x ) FEATURE:
        ( A ) NAME/KEY: phakellistatin 11
              ( c ) IDENTIFICATION METHOD: by experiment using
              amino acid analysis, high resolution
              nuclear magnetic resonance and mass
              spectral MS/MS techniques
        ( D ) OTHER INFORMATION: Phakellistatin is a
              cell growth inhibitory peptide with
              activity in murine lymphocytic leukemia
              cell line of 0.20 mg/mL ( x i ) SEQUENCE DESCRIPTION: SEQ ID NO: 2:

Pro Gln Pro Phe Pro Phe Ile Phe
        1               5
```

ISOLATION AND STRUCTURE OF THE HUMAN CANCER CELL GROWTH INHIBITORY CYCLIC OCTAPEPTIDES PHAKELLISTATIN 10 AND 11

The invention relates generally to the field of agents which may be potentially useful in the field of chemotherapy. More particularly, this invention relates to the discovery of two new cyclic octapeptides, which have been shown to be cytostatic in vitro, designated herein as phakellistatin 10, and phakellistatin 11.

This research was funded in part by Outstanding Investigator Grant CA 44344-01-06 awarded by the National Cancer Institute, DHHS. The United States government may have certain rights to this invention.

BACKGROUND OF THE INVENTION

In a designated series of compounds, either those initially extracted from the same sponge or those which are chemically related to a compound which was earlier extracted from a different species of the same genus, the same system of nomenclature needs to be used. Compounds of the same series are generally numbered in cardinal order.

Several compounds which may be useful in the treatment of one or more neoplastic diseases through chemotherapy have already been isolated from the Western Pacific Ocean marine sponge Phakellia sp. These compounds include the cyclic heptapeptide previously denominated as phakellistatin 4, and several decapeptides.

BRIEF SUMMARY OF THE INVENTION

To date, many promising compounds have been developed from marine animals in general, and in particular Porifera indigenous to tropical areas. This is, in part, believed to be the lack of natural defenses possessed by such organisms, which requires them to protect themselves biochemically. Additionally, such organisms generally have extremely low incidences of neoplastic diseases.

As is well known in the art, most compounds fail to demonstrate a distinctive "mean graph". Both compounds disclosed herein, phakellistatin 10, and phakellistatin 11, display distinctive mean graphs. These mean graphs are highly similar to each other, with a correlation coefficient of 0.96.

As the included data demonstrate, phakellistatin 10 attained an $LC_{50}$ of less than $10^{-5}M$ per milliliter against the MDA-MB-435 breast cancer cell line. It also achieved Total Growth Inhibition ("TGI") for two breast cancer and two CNS cancer cell lines at a concentration of less than $10^{-6}M$ per milliliter.

The included data for phakellistatin 11 shows a moderately higher level of in vitro activity as shown by an $LC_{50}$ of less than $10^{-5}M$ per milliliter against the MDA-MB-435 breast cancer cell line and five other cell lines. It also achieved total growth inhibition for two breast cancers, one CNS cancer, one ovarian cancer, and one non-small cell lung cancer cell lines at a concentration of less than $10^{-7}M$ per milliliter.

Accordingly, the primary object of the subject invention is the isolation of two new cyclic octapeptides which have been shown to be cytostatic in vitro and are designated herein as phakellistatin 10, and phakellistatin 11.

DESCRIPTION OF THE PREFERRED EMBODIMENT

The importance of the subject invention is the pharmacological effects of the compounds disclosed herein. Accordingly, a brief explanation of the statistical measures employed in evaluating this activity is appropriate.

The following measures are used to express drug activity by giving the drug dose which reduces cell growth to a specified percentage of growth:

$ED_{50}$ (P388) and $GI_{50}$ (HTCL) are the drug doses needed to reduce the percent growth to 50%. There is no mathematical difference between $ED_{50}$ and $GI_{50}$, which are both calculated using the same formula. The only difference is historical usage.

Total Growth Inhibition ("TGI") is the drug dose needed to yield zero percent growth, i.e., just as many cells at the end of the experiment as were present in the beginning. Whether just as many cells were killed as were produced (steady state), or no growth occurred (total inhibition), cannot be distinguished.

Lethal Concentration 50% ("$LC_{50}$") is the drug concentration which reduces growth to −50%, i.e., removes half of the cells originally present at the beginning of the experiment.

Each drug is tested at five (5) doses: 100-10-1-0.1-0.01 µg/ml. Percent Growths are calculated for each dose. The two (or three) doses with growth values above, below, (or near to) 50% growth are used to calculate the $ED_{50}/GI_{50}$ using a linear regression formula. The log of the dose is used during the regression computation. If no dose yields a growth value under 50%, the results are expressed as: $ED_{50}$>(highest dose). If no dose yields growth higher than 50% growth, then $ED_{50}$<(lowest dose). Similar calculations are performed for the TGI at 0% growth, and at −50% growth for the $LC_{50}$.

PERCENT OF GROWTH

At the start of an experiment, cells from the in vitro cell cultures are inoculated into the appropriate tubes or microtiter plates. One set of control tubes/plates is immediately counted to determine the number of cells at the start of the experiment. This is the "baseline count", or "$T_{zero}$ reading". At the end of the experiment (48 hours later) a second set of control tubes/plates is analyzed to determine the "Control Growth" value. The growth (or death) of cells relative to the initial quantity of cells is used to define the "Percent of Growth".

| | EXAMPLE: |
|---|---|
| | Baseline Count = 20 |
| | Control Count = 200 |
| | (10-Fold Growth) |
| 100% Growth = Control Growth | 100% Growth = 200 |
| 50% Growth = $T_{zero}$ + Control-$T_{zero}$/2 | 50% Growth = 110 |
| 0% Growth = $T_{zero}$ | 0% Growth = 20 |
| −50% Growth = $T_{zero}$/2 | −50% Growth = 10 |

For further information about the testing protocols and procedures see Anne Monks et al., "Feasibility of a High-Flux Anticancer Drug Screen Using a Diverse Panel of Cultured Human Tumor Cell Lines", 83 *J. Nat. Cancer Inst.* No. 11, pp. 757–66 (5 June 1991) and Michael J. Boyd, "Status of the NCI Preclinical Antitumor Drug Discovery Screen", 3 *Princ. & Practice of Oncology Updates* No. 10, pp. 1–12 (October 1989).

In 1986–7 the yellow-orange Phakellia sp. (class Demospongiae, order Axinellida) was collected (500 kg wet wt) at −25 to −40 m (in very strong current locations, 1.75–2.75 kph) in the Truk Archipelago of the Federated States of Micronesia (Chuuk). An initial methanol/sea water extract was concentrated and separated by a solvent partition and gel permeation (SEPHADEX LH-20) sequence. Further separation (P388 bioassay guided) was accomplished using partition column chromatography (SEPHADEX LH-20) employing successively: hexane-dichloromethane-methanol 5:5:1; hexane-toluene-methanol 3:1:1; and hexane-2-propanol-methanol 8:1:1 as eluents. Final separation was realized by reversed-phase HPLC (C8 column, methanol-acetonitrile-water 3:3:4 and 2:3 acetonitrile-water as eluents). See the separation scheme below.

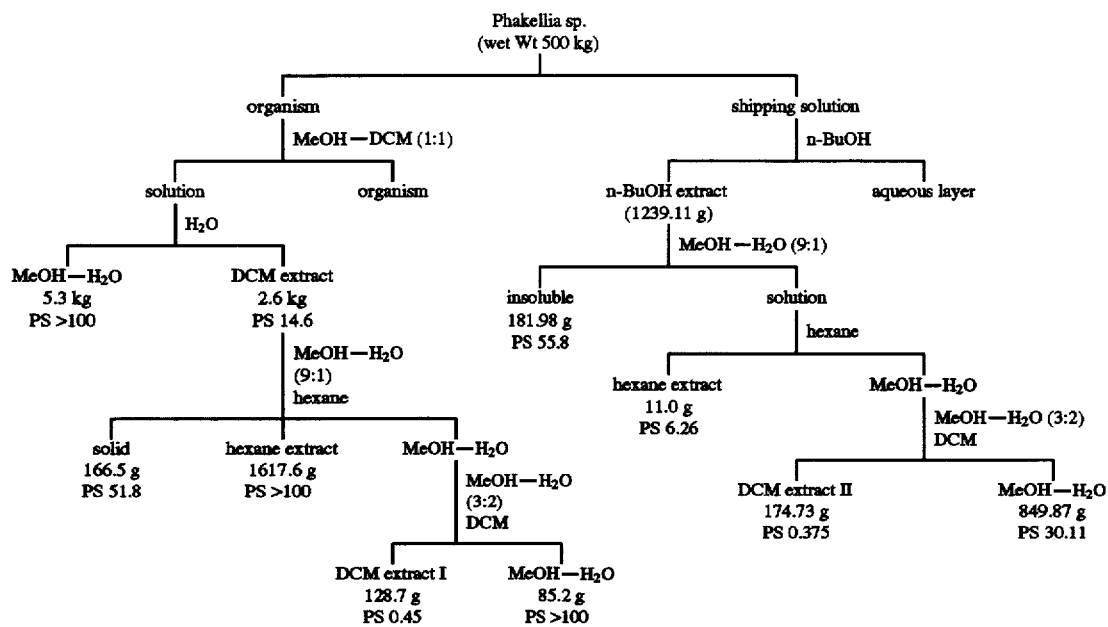

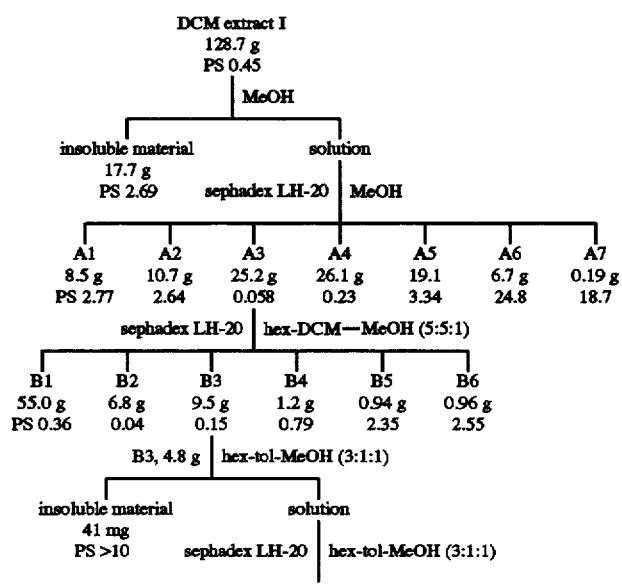

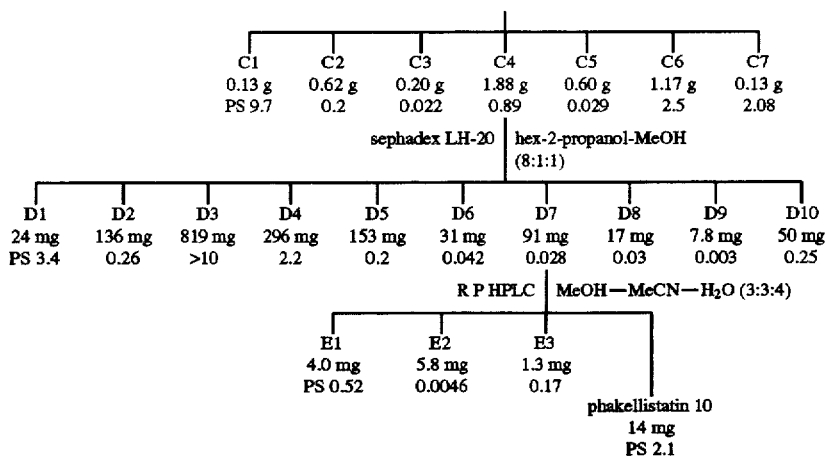
-continued
Separation Scheme Part 2
*PS = P388 ED$_{50}$ in µg/ml
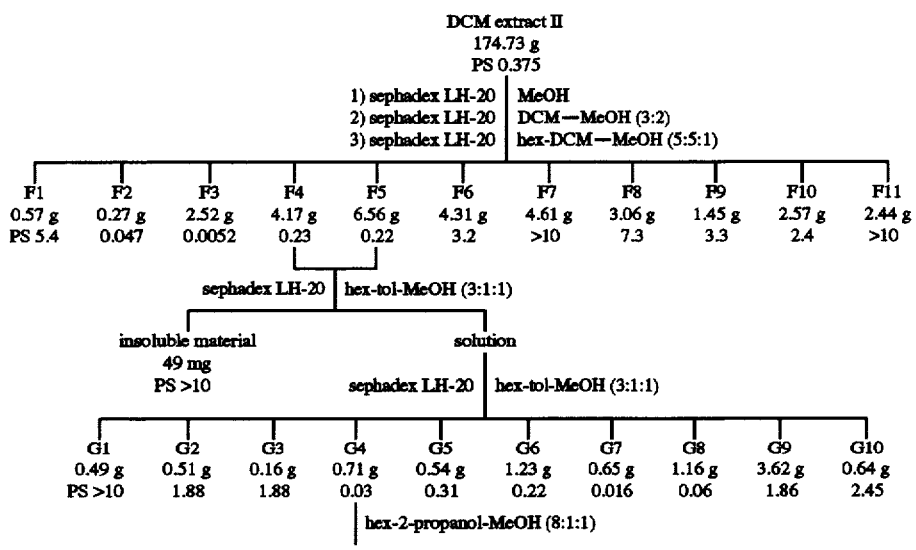
Separation Scheme Part 3

-continued
Separation Scheme Part 3

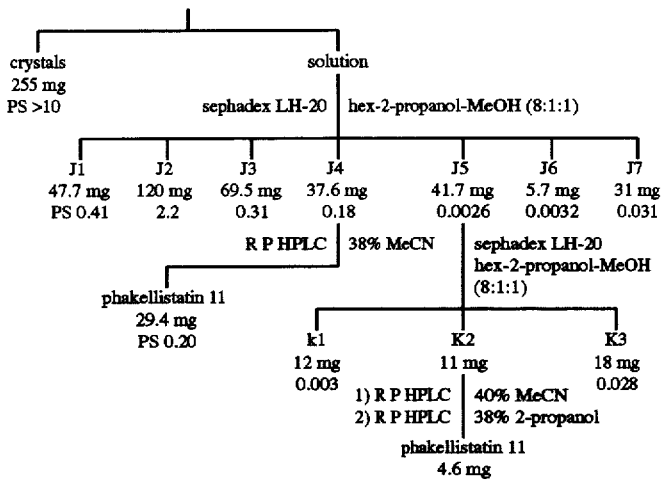

*PS = P388 ED₅₀ in μg/ml

Phakellistatin 10 (1), 14 mg, yield 5.6×10⁻⁶%) was obtained as a colorless amorphous powder from methanol, mp 217°–219° C.; $[\alpha]_D^{25}$ −128° (c=0.19 in CH$_3$OH). Phakellistatin 11 (2), 34 mg, yield 6.8×10⁻⁶%) was also isolated as a colorless amorphous solid, mp 194°–196° C.; $[\alpha]_D^{25}$ −1630 (c=0.08 in CH$_3$OH).

The high field (500 MHz) 2D ¹H-NMR, APT and HMQC and ¹³C-NMR spectra (in CD$_2$Cl$_2$, Table 1) of phakellistatin 10 (1) indicated the presence of seven CH$_3$, twelve CH$_2$, three C—CH—C, and nine C—CH—X groups as well as eight aromatic carbons and four separated carbonyl signals which suggested that phakellistatin 10 (1) was a peptide with a tryptophan unit. Extensive application of H¹,H¹ COSY and HMBC techniques were used for further structure determination. A low field methyl signal (δ1.10, d) was attributed to a threonine unit, two methyls (δ0.45, d, J=4.5; δ0.80, d, J=8.0) to an isoleucine unit, the methyls at δ0.76 (d, J=6.5) and 0.87 (d, J=6.0) to valine and two at δ0.79 (d, J=7.0) and 0.87 (d, J=6.0) to leucine. Three —CH$_2$—CH$_2$—CH$_2$— chains corresponding to proline were uncovered. The existence of tryptophan was recognized by a moderate absorption at 281 nm in the UV spectrum.

High resolution FAB mass measurements of the protonated molecular ion of phakellistatin 10 (1) resulted in an exact mass of m/z 904.5271 corresponding to a molecular formula of C$_{47}$H$_{70}$N$_9$O$_9$ (theoretical 904.5297) and indicated a cyclic peptide structure. Tandem mass spectrometry of the [M+H]⁺ ion of m/z 904 produced a number of lower mass fragment ions which were the immonium ions of the amino acids present in the peptide. The presence of these ions of m/z 70 (Pro), 72 (Val), 74 (Thr), 86 (Leu or Ile) and 159 (Trp), when combined with the exact mass and NMR information established the amino acid content as 3×Pro, 2×Leu or Ile, Val, Thr and Trp. Protonation at each of the three proline residues followed by ring opening produced three different acyllium ions. The position of the Leu and Ile residues was established by the presence of low abundance ions at m/z 466 and 523 that involve fragmentation of the amino acid side chain. The acyllium ions, formed by fragmentation at the amide bonds, can undergo further decomposition to eliminate CO. Such fragment ions that have either Leu or Ile at the C-terminus can undergo further degradation to eliminate C$_3$H$_6$ (−42u) in the case of Leu or C$_2$H$_4$ (−28u) in the case of Ile. The amino acid sequence of phakellistatin 10 (1) was determined to be cyclo-(Pro-Leu-Thr-Pro-Ile-Pro-Trp-Val), SEQ ID NO:1.

Structural elucidation of phakellistatin 11 (2) was also achieved by 2D NMR and HRFABMS analyses. The high-resolution FABMS (m/z 974.5135 [M+H]⁺, Δ+0.5 ppm) established the molecular formula as C$_{53}$H$_{67}$N$_9$O$_9$ (theoretical 974.5140). The ¹H-NMR spectrum of phakellistatin 11 (2) in deuterodimethylsulfoxide showed signals between 7.46 ppm and 8.72 ppm (amide protons which were not visible in deuteromethanol) suggesting a peptide. Amino acid analysis showed the presence of Pro (3×), Phe (3×), Ile, and Gln units. The twenty-five sites of unsaturation required by the molecular formula and a negative reaction to the ninhydrin-collidine reagent indicated a cyclic peptide.

The amino acid sequence of cyclic peptide (2) was first determined by HMBC and ROESY experiments. The fragment of residues 1 to 5 of SEQ ID NO: 2, i.e., the -Pro¹-Gln²-Pro³-Phe⁴-Pro⁵-segment, was deduced by correlations between NH (Gln²)/CO (Pro) and NH (Phe⁴)/CO (Pro⁵) in the HMBC spectrum and by noe connection between δ-H2 (Pro³) and α-H (Gln²) in the ROESY spectrum (in DMSO-d$_6$). The chemical shift difference (Δδ4.11 ppm) between the β- and γ-carbons in Pro³ indicated a trans Gln²-Pro³ amide bond. The -Phe⁶-Ile⁷-Phe⁸ sequence was suggested by HMBC cross peaks between NH (Ile⁷)/CO (Phe⁶), α-H (Ile⁷)/CO (Phe⁶) and NH (Phe8)/CO (Ile) in DMSO-d$_6$. In addition, the HMBC spectrum in CD$_3$CN showed a cross signal for NH (Phe⁶) and CO (Pro⁵). Thus, the structure of phakellistatin 11 (2) was determined to be cyclo-(Pro-Gln-Pro-Phe-Pro-Phe-Ile-Phe), SEQ ID No:2. When combined with the data on immonium ions produced in tandem mass spectrometry experiments the amino acid content established by NMR was confirmed. Furthermore, upon collisional activation, the [M+H]⁺ ions of phakellistatin 11 (2) fragments by a route that confirmed the amino acid sequence to be cyclo-(Pro-Gln-Pro-Phe-Pro-Phe-Ile-Phe), SEQ ID NO:2.

The absolute configurations of both peptides were elucidated by chiral GC analysis of the N-perfluoropropionyl isopropyl ester derivatives of the peptide hydrolysates. Except for tryptophan (which decomposed during the acid hydrolysis) all of the amino acids were found to possess the (S)-configuration.

Cyclic peptides (1) and (2) were tested ($10^{-5}$M high test concentration; $\log_{10}$ dilutions) in the NCI's 60-cell line human tumor in vitro screen, and a variety of data analyses were performed. Phakellistatins 10 (1) and 11 (2) gave overall panel-averaged $GI_{50}$ concentrations of $7.90\pm2.63\times 10^{-7}$M, and $1.32\pm0.49\times 10^{7}$M, respectively. TGI-COMPARE correlation analyses of the differential cytotoxicity profile of cyclic octapeptide (1) showed Pearson correlation coefficients of 0.81, 0.96 and 0.77 with the profiles of phakellistatin 4, phakellistatin 11 (2), and the standard agent vinblastine, respectively. Likewise, similar analyses of the profile of cyclic octapeptide (2) showed Pearson correlation coefficients of 0.83, 0.96 and 0.87 with the profiles of phakellistatin 4, phakellistatin 10 (1) and vinblastine, respectively. These similarities in screening results as shown by the high TGI-COMPARE correlations reflect a similarity in biological properties and/or chemical structure and properties. See K. D. Paull et al., "Display and Analysis of Patterns of Differential Activity of Drugs Against Human Tumor Cell Lines: Development of Mean Graph and COMPARE Algorithm", 81 *J. Nat. Cancer Institute* No. 14, pp. 1088–92 (Jun. 5, 1991).

Interestingly, phakellistatin 10 (1) is the Pro-Ile-Pro counterpart of the hymenamide Pro-Leu-Pro sequence. Hymenistatin 1 bears the same (Ile vs. Leu) relationship to hymenamide G. This suggests that these cell growth inhibitory cyclic peptides have a common microorganism genesis or are growth regulatory/defensive substances produced by closely related marine Porifera.

The structures of these compounds are as shown below:

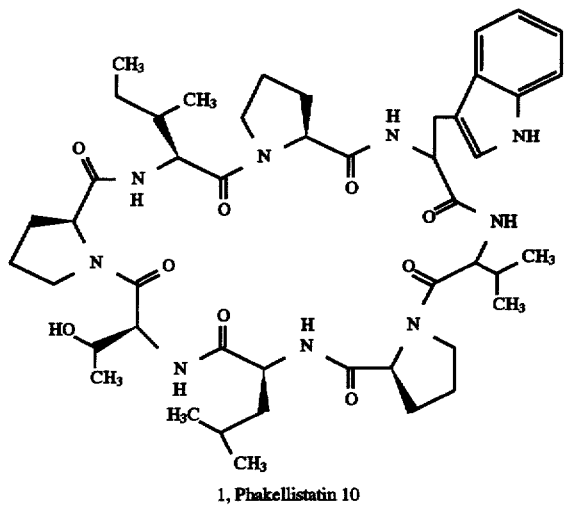

1, Phakellistatin 10

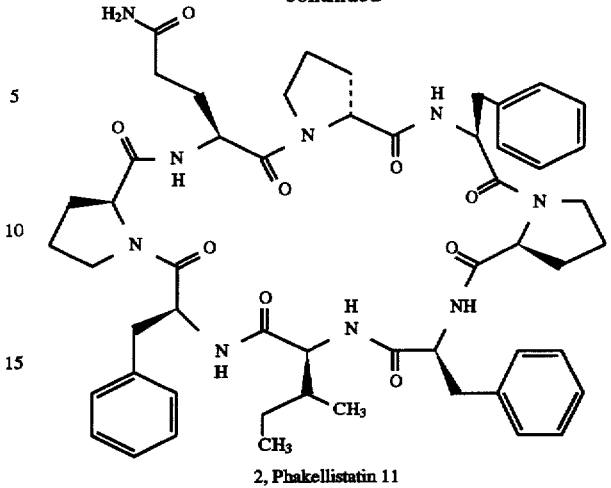

2, Phakellistatin 11

Based upon the foregoing these compositions are believed useful in the treatment of one or more neoplastic diseases. For example, acute myelocytic leukemia, acute lymphocytic leukemia, malignant melanoma, adenocarcinoma of lung, neuroblastoma, small cell carcinoma of the lung, breast carcinoma, colon carcinoma, ovarian carcinoma, bladder carcinoma, and the like.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch.

Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies either the compound designated herein as phakellistatin 10 or the compound designated herein as phakellistatin 11.

COMPOSITION "A"

Hard-Gelatin Capsules

One thousand two-piece hard gelatin capsules for oral use, each capsule containing 200 mg of an active ingredient are prepared from the following types and amounts of ingredients:

| | |
|---|---|
| Active ingredient, micronized | 200 g |
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 50, 250 and 500 mg amounts by substituting 50 g, 250 g and 500 g of an active ingredient for the 200 g used above.

COMPOSITION "B"

Soft Gelatin Capsules

One-piece soft gelatin capsules for oral use, each containing 200 mg of an active ingredient, finely divided by means of an air micronizer, are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

COMPOSITION "C"

Tablets

One thousand tablets, each containing 200 mg of an active ingredient, are prepared from the following types and amounts of ingredients:

| | | |
|---|---|---|
| Active ingredient, micronized | 200 g | |
| Lactose | 300 g | |
| Corn starch | 50 g | |
| Magnesium stearate | 4 g | |
| Light liquid petrolatum | 5 g | |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing an active ingredient in 250 mg and 100 mg amounts by substituting 250 g and 100 g of an active ingredient for the 200 g used above.

COMPOSITION "D"

Oral Suspension

One liter of an aqueous suspension for oral use, containing in each teaspoonful (5 ml) dose, 50 mg of an active ingredient, is prepared from the following types and amounts of ingredients:

| | | |
|---|---|---|
| Active ingredient, micronized | 10 g | |
| Citric acid | 2 g | |
| Benzoic acid | 1 g | |
| Sucrose | 790 g | |
| Tragacanth | 5 g | |
| Lemon Oil | 2 g | |
| Deionized water, q.s. 1000 ml | | |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

COMPOSITION "E"

Parenteral Product

A sterile aqueous suspension for parenteral injection, containing 30 mg of an active ingredient in each milliliter for treating a neoplastic disease, is prepared from the following types and amounts of ingredients:

| | | |
|---|---|---|
| Active ingredient, micronized | 30 g | |
| POLYSORBATE 80 | 5 g | |
| Methylparaben | 2.5 g | |
| Propylparaben | 0.17 g | |
| Water for injection, q.s. 1000 ml. | | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 ml) three times a day.

COMPOSITION "F"

Suppository, Rectal and Vaginal

One thousand suppositories, each weighing 2.5 g and containing 200 mg of an active ingredient are prepared from the following types and amounts of ingredients:

| | | |
|---|---|---|
| Active ingredient, micronized | 15 g | |
| Propylene glycol | 150 g | |
| Polyethylene glycol #4000, q.s. | 2,500 g | |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

COMPOSITION "G"

Intranasal Suspension

One liter of a sterile aqueous suspension for intranasal instillation, containing 20 mg of an active ingredient in each milliliter, is prepared from the following types and amounts of ingredients:

| | | |
|---|---|---|
| Active ingredient, micronized | 15 g | |
| POLYSORBATE 80 | 5 g | |
| Methylparaben | 2.5 g | |
| Propylparaben | 0.17 g | |
| Deionized water, q.s. 1000 ml. | | |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

COMPOSITION "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

One hundred grams of an active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

COMPOSITION "J"

Insufflation

One hundred grams of an active ingredient in bulk form is finely divided by means of an air micronizer.

The foregoing composition is useful for treating a neoplastic disease, by the inhalation of 300 mg one to four times day.

From the foregoing, it becomes readily apparent that a new and useful antineoplastic agent and new and useful antineoplastic reparations have been herein described and illustrated which fulfill the aforestated objects in a remarkably unexpected fashion. It is, of course, understood that such modifications, alterations and adaptions as will readily occur to the artisan confronted with this disclosure are intended within the spirit of the present invention which is limited only by the scope of the claims appended hereto.

---

Accordingly, what is claimed is:

1. A compound denominated herein as phakellistatin 10 and having the structure set forth below:

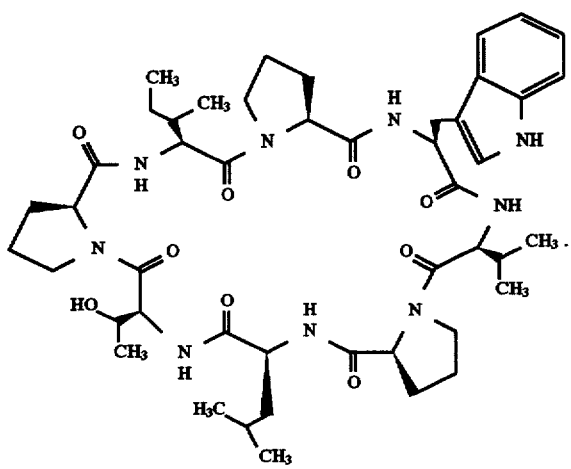

2. A compound according to claim 1 which is pure.

3. A compound denominated herein as phakellistatin 11 and having the structure set forth below:

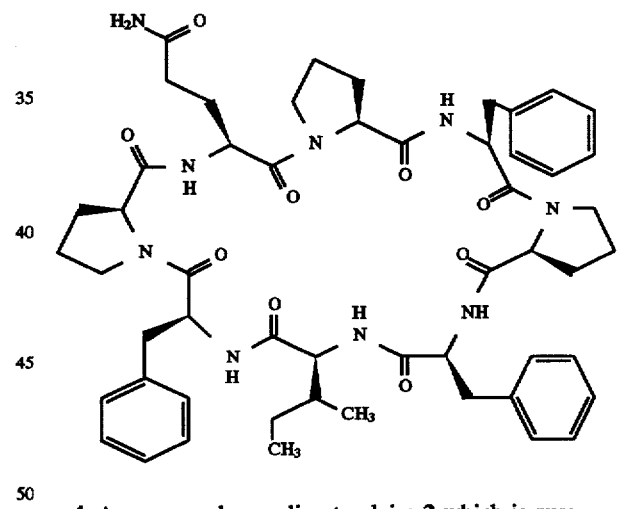

4. A compound according to claim 3 which is pure.

* * * * *